US010001399B2

(12) United States Patent
Grass

(10) Patent No.: US 10,001,399 B2
(45) Date of Patent: Jun. 19, 2018

(54) REDUCING AGENT TANK

(71) Applicant: CONTINENTAL AUTOMOTIVE GMBH, Hannover (DE)

(72) Inventor: Phillippe Grass, Regensburg (DE)

(73) Assignee: Continental Automotive GmbH, Hannover (DE)

(*) Notice: Subject to any disclaimer, the term of this patent is extended or adjusted under 35 U.S.C. 154(b) by 0 days. days.

(21) Appl. No.: 14/654,412

(22) PCT Filed: Dec. 10, 2013

(86) PCT No.: PCT/EP2013/076111
§ 371 (c)(1),
(2) Date: Jun. 19, 2015

(87) PCT Pub. No.: WO2014/095496
PCT Pub. Date: Jun. 26, 2014

(65) Prior Publication Data
US 2016/0195421 A1    Jul. 7, 2016

(30) Foreign Application Priority Data
Dec. 20, 2012 (DE) .......... 10 2012 224 095

(51) Int. Cl.
*G01F 23/296* (2006.01)
*F01N 3/20* (2006.01)
*G01N 27/07* (2006.01)

(52) U.S. Cl.
CPC ......... *G01F 23/296* (2013.01); *F01N 3/2066* (2013.01); *G01N 27/07* (2013.01);
(Continued)

(58) Field of Classification Search
CPC ..... F01N 2900/1806; F01N 2900/1814; F01N 3/2066; F01N 2610/142; F01N 2610/148;
(Continued)

(56) References Cited

U.S. PATENT DOCUMENTS 3,252,885 A * 5/1966 Griswold ............... B01D 35/06
204/665
5,209,275 A * 5/1993 Akiba ..................... B67D 7/342
141/192
(Continued)

FOREIGN PATENT DOCUMENTS

CN  102 575 560  7/2012
CN  102 667 085  9/2012
(Continued)

*Primary Examiner* — Manish S Shah
*Assistant Examiner* — Suman K Nath
(74) *Attorney, Agent, or Firm* — Cozen O'Connor

(57) ABSTRACT

A reducing agent tank for receiving and storing a reducing agent solution, with a filler pipe and a fill level sensor for determining the level of the aqueous reducing agent solution in the reducing agent tank. In order to create a reducing agent tank for receiving and storing an aqueous reducing agent solution that allows storage of the liquid pollutant-reducing medium and simultaneously enables reliable detection of incorrect filling of the tank, a first electrode and a second electrode are arranged in the filler pipe such that a liquid flowing into the reducing agent tank flows over the first electrode and a second electrode, the first electrode and the second electrode coming into direct contact with the inflowing liquid.

8 Claims, 2 Drawing Sheets

(52) U.S. Cl.
CPC .... *F01N 2610/02* (2013.01); *F01N 2610/142* (2013.01); *F01N 2610/148* (2013.01); *F01N 2610/1413* (2013.01); *F01N 2900/1806* (2013.01); *F01N 2900/1814* (2013.01); *Y02T 10/24* (2013.01)

(58) Field of Classification Search
CPC ......... F01N 2610/1413; F01N 2610/02; Y02T 10/24; G01F 23/296; G01N 27/07
USPC ........................ 73/61.61; 340/603, 618, 620
See application file for complete search history.

(56) References Cited

U.S. PATENT DOCUMENTS

| | | | | |
|---|---|---|---|---|
| 6,408,619 | B1 * | 6/2002 | Wissler | B01D 53/8696 60/286 |
| 8,146,404 | B1 * | 4/2012 | Griffin | G01N 1/24 250/282 |
| 8,319,654 | B2 * | 11/2012 | Field | A47L 13/26 204/194 |
| 9,038,374 | B2 | 7/2015 | Brueck et al. | |
| 2007/0175805 | A1 * | 8/2007 | McKinney | C02F 1/686 210/87 |
| 2009/0314651 | A1 | 12/2009 | Field | |
| 2010/0199781 | A1 * | 8/2010 | Colby | G01F 1/7088 73/861.09 |
| 2013/0074590 | A1 * | 3/2013 | Bertow | F01N 3/2066 73/114.71 |
| 2015/0314677 | A1 * | 11/2015 | Booth | B60K 15/04 220/562 |

FOREIGN PATENT DOCUMENTS

| | | | |
|---|---|---|---|
| DE | 198 41 770 | 4/2000 | |
| DE | 20 2009 009647 | 10/2009 | |
| DE | 20 2009 006151 | 10/2010 | |
| DE | 10 2010 042386 | 4/2012 | |
| EP | 0 816 284 | 1/1998 | |
| EP | 2 458 171 | 5/2012 | |
| WO | WO 2011064050 A1 * | 6/2011 | ........... F01N 3/2066 |
| WO | WO 2011/101016 | 8/2011 | |

* cited by examiner

REDUCING AGENT TANK

CROSS REFERENCE TO RELATED APPLICATIONS

This is a U.S. national stage of application No. PCT/EP2013/076111, filed on Dec. 10, 2013. Priority is claimed on German Application No.: DE102012224095.0, filed Dec. 20, 2012, the content of which is incorporated herein by reference.

BACKGROUND OF THE INVENTION

1. Field of the Invention

The invention relates to a reducing agent tank for receiving and storing a reducing agent solution, having a filler neck and a fill level sensor for determining the fill level of the reducing agent solution in the reducing agent tank.

2. Detailed Description of the Prior Art

For the reduction of a nitrogen oxide fraction in the exhaust gas of an internal combustion engine, exhaust-gas aftertreatment may be performed using an aqueous reducing agent solution. The aqueous reducing agent solution may be referred to as a reducing agent. The reducing agent is preferably urea. For the exhaust-gas aftertreatment, the aqueous reducing agent solution is pumped, by way of a liquid pump, to a reducing agent injection valve that meters the reducing agent solution into an exhaust-gas flow in an exhaust tract of the internal combustion engine upstream of the SCR catalytic converter. A specially designed reducing agent tank is used to store the reducing agent. A situation may arise in which the reducing agent tank is filled not with the aqueous reducing agent solution but with another liquid, such as fuel or oil. Such misfilling of the reducing agent tank would lead to severe damage to the exhaust-gas aftertreatment system and must be reliably detected in order that relevant protective measures can be initiated. A protective measure after misfilling of the reducing agent tank could be a deactivation of the exhaust-gas aftertreatment system, a corresponding entry in the fault memory of the engine controller, and/or a warning message to the driver of the vehicle.

SUMMARY OF THE INVENTION

An object of the invention is providing a reducing agent tank for receiving and storing a reducing agent solution, which reducing agent tank permits storage of the liquid pollutant-reducing medium and simultaneously permits reliable detection of misfilling.

In one embodiment of the invention a first electrode and a second electrode are arranged in the filler neck such that a liquid flowing into the reducing agent tank flows over the first electrode and the second electrode. The first electrode and the second electrode come into direct contact with the inflowing liquid. This has the advantage that the process of the filling of the reducing agent tank is reliably detected by the fill level sensor. Misfilling of the reducing agent tank can be identified by way of the direct contact of the liquid with the first electrode and the second electrode. Reducing agent solutions are media that exhibit good conductivity for electrical current, whereas fuel and oil scarcely conduct electrical current. Thus, if the fill level sensor detects the process of the reducing agent tank being filled, but no electrical current can flow between the first electrode and the second electrode, this is a clear indication of misfilling of the reducing agent tank. The above-described protective measures can thus be immediately initiated.

The reducing agent tank according to one embodiment of the invention may be produced by an injection molding process in which the first electrode and the second electrode are arranged as a prefabricated module in the tank wall in the region of the filler neck. The reducing agent tank may be substantially plastic.

In an advantageous refinement, the first electrode is a first metallic mesh. The inflowing liquid can pass unhindered through the metallic mesh, wherein solid contaminants, such as grains of sand, are filtered out. Since a mesh of this type can be formed over a large area and, ideally, spans the entire cross section of the filler neck, it is ensured that the liquid flowing into the reducing agent tank comes into direct contact with the first electrode. If the second electrode is a second metallic mesh, the above statements also apply to the second electrode.

In a further advantageous refinement, the fill level sensor is in an ultrasonic fill level sensor. Ultrasonic fill level sensors are extremely well suited to the reliable and precise determination of the fill level of the reducing agent solution in the reducing agent tank.

BRIEF DESCRIPTION OF THE DRAWINGS

Exemplary embodiments of the invention will be discussed below on the basis of the drawings, in which.

Elements of identical design or function are denoted by the same reference signs throughout the figures.

DETAILED DESCRIPTION OF THE PRESENTLY PREFERRED EMBODIMENTS

A reducing agent tank 1 for storing a liquid medium for the reduction of pollutants in exhaust gases may be arranged in a motor vehicle. The liquid medium for the reduction of pollutants may preferably be an aqueous reducing agent solution 2 and/or a reducing agent precursor, for example an aqueous urea solution.

Figure 1:
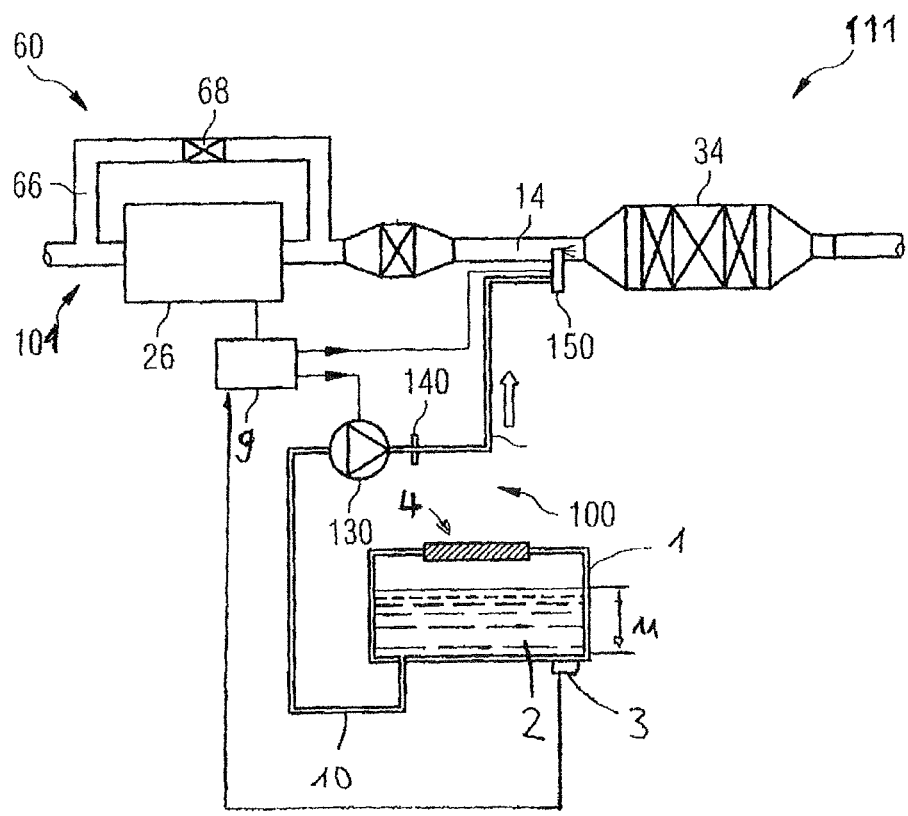
FIG. 1 is an exhaust-gas aftertreatment system.

FIG. 1 shows an exhaust-gas aftertreatment system 111 having an intake tract 101, a combustion chamber 26, an exhaust tract 14, an exhaust-gas recirculation arrangement 60, and a reducing agent supply system 100.

An electronic control unit 9 monitors the functions of the exhaust-gas aftertreatment system 111.

The exhaust-gas recirculation arrangement 60 has an exhaust-gas recirculation line 66. The exhaust-gas recirculation line 66 branches off from the exhaust tract 14 downstream of the combustion chamber 26 and opens into the intake tract 101 upstream of the combustion chamber 26. In the exhaust-gas recirculation line 66 there is arranged an exhaust-gas recirculation valve 68 by which the recirculated exhaust-gas flow rate can be controlled. Via the exhaust-gas recirculation line 66, exhaust gas can be recirculated into the combustion chamber 26 of the internal combustion engine to thereby reduce the oxygen content in the inducted gas mixture intended for the combustion chamber 26, and thus reduce the emissions of nitrogen oxides.

A catalytic converter 34 for selective catalytic reduction (SCR catalytic converter) is arranged in the exhaust tract. An, oxidation catalytic converter arranged in the exhaust tract 14 can oxidize NO emerging from the SCR catalytic converter 34 to form $NO_2$.

The exhaust tract 14 is preferably assigned the reducing agent supply system 100. The reducing agent supply system 100 comprises a reducing agent tank 1 for receiving the reducing agent solution 2. The reducing agent supply system 100 furthermore has various hydraulic assemblies such as, for example, a reducing agent pump 130, a pressure regulating valve 140, and a reducing agent injection valve 150. By the reducing agent pump 130, the reducing agent can be conducted from the reducing agent tank 1 via a reducing agent line 10 to the reducing agent injection valve 150. Through corresponding control of the reducing agent injection valve 150, the reducing agent 2 can then be metered into the exhaust gas in the exhaust tract 14, wherein the injection direction may be oriented either in the direction of the exhaust-gas flow or in the direction opposed to the exhaust-gas flow. The pumping of the reducing agent 2 from the reducing agent tank 1 to the reducing agent injection valve 150 is conducive to advantageous metering of the reducing agent 2.

A control unit 9 may be designed to control dosing of the reducing agent 2 in a manner dependent on measured values detected in the combustion chamber and/or in the reducing agent. If filling of the reducing agent tank with an incorrect liquid 12 is detected, the control unit 9 can stop the supply of the reducing agent solution 2 to the reducing agent injection valve 150 by deactivating the reducing agent pump 130.

To permit the most precise possible dosing of the reducing agent 2, it is possible for one or more parameters, for example the reducing agent concentration or the fill level 11 of the reducing agent 2 in the reducing agent tank 1, to be detected. A change in the reducing agent concentration may result from a decomposition reaction of the reducing agent solution 2 and/or an increasing concentration dive to evaporation of the water fraction in the reducing agent solution 2. To detect the respective parameters, one or more sensors may be arranged in and/or on the reducing agent tank 1. To detect the fill level 11 of the reducing agent 2, a fill level sensor 3 is arranged in or on the reducing agent tank 1. The fill level sensor 3 is electrically connected to the control unit 9.

Figure 2:
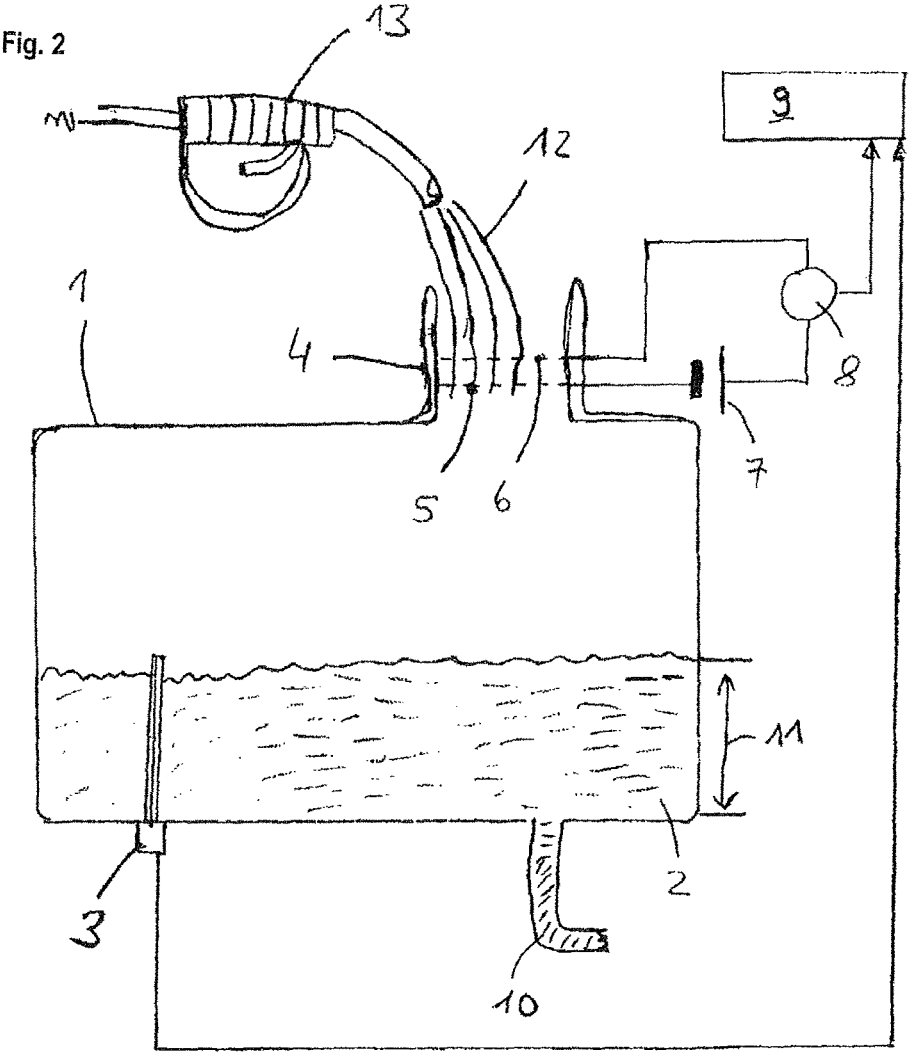
FIG. 2 is a reducing agent tank.

FIG. 2 shows a reducing agent tank 1 designed for storing a reducing agent solution 2. The reducing agent tank 1 is filled with the reducing agent solution 2 via the filler neck 4. The reducing agent tank 1 has a fill level sensor 3 by which the fill level 11 of the reduCing agent solution 2 in the reducing agent tank 1 can be determined. The fill level sensor 3 is electrically connected to a control unit 9. Furthermore, FIG. 2 shows the reducing agent line 10 formed on the reducing agent tank 1, through which reducing agent line the aqueous reducing agent solution 2 can be supplied into the SCR catalytic converter 34.

The reducing agent tank 1 is filled via the filler neck 4. Here, a situation may arise in which misfilling of the tank occurs, for example by a filling nozzle 13 for a fuel being inserted into the filler neck 4 of the reducing agent tank 1. Thus, a liquid 12 not intended for use as reducing agent solution 2 flows into the reducing agent tank 1 from the filling nozzle 13. Such misfilling of the reducing agent tank 1 must be reliably detected to prevent damage to the exhaust-gas aftertreatment system 111. For this purpose, a first metallic electrode 5 and a second metallic electrode 6 are formed in the filler neck 4, which electrodes are positioned in the filler neck 4 such that the inflowing liquid 12 flows over them, and said electrodes come into direct contact with the inflowing liquid 12.

During filling of the reducing agent tank 1, the fill level sensor 3 will detect a change in the fill level of the reducing agent solution 2. The change in the fill level 11 is signaled to the control unit 9 by the fill level sensor 3. Furthermore, between the first metallic electrode 5 and the second metallic electrode 6, there is connected a measurement device 8, which measures the current that can flow via the inflowing liquid 12. If the inflowing liquid 12 exhibits a low resistance it allows a high current to flow, and it can be inferred from this that the reducing agent tank has been filled with an aqueous reducing agent solution, whereby misfilling has not occurred. However, if the inflowing liquid 12 is a fuel or an engine oil, only a very low current will be able to flow via such liquids, as the resistance of such liquids is very high. This is detected by the measurement device 8 and transmitted to the control unit 9. If the control unit 9 detects a rising fill level 11 and receives information to the effect that the resistance of the inflowing liquid is high, then the control unit can reliably detect misfilling of the reducing agent tank 1 and initiate corresponding countermeasures for the protection of the exhaust-gas aftertreatment system 111.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A plastic reducing agent tank configured to receive and store a reducing agent solution, comprising:
   a plastic filler neck;
   a fill level sensor that determines a fill level of the reducing agent solution in the reducing agent tank; and
   a first electrode and a second electrode each affixed in the filler neck by an injection molding process and each arranged transverse to a filling direction such that an inflowing liquid flowing into the reducing agent tank flows through the first electrode and the second electrode,
   wherein the first electrode and the second electrode come into direct contact with the inflowing liquid to measure a conductivity of the inflowing liquid, and
   wherein the first electrode is a first metallic mesh configured to filter solid contaminants from the inflowing liquid.

2. The reducing agent tank as claimed in claim 1, wherein the fill level sensor is an ultrasonic fill level sensor.

3. The reducing agent tank as claimed in claim 1, wherein the second electrode is a second metallic mesh.

4. The reducing agent tank as claimed in claim 3, wherein the first and second electrodes span an entire cross section of the filler neck.

5. The reducing agent tank as claimed in claim 1, wherein the first and second electrodes span an entire cross section of the filler neck.

6. The reducing agent tank as claimed in claim 1, wherein the fill level sensor is configured to output a signal indicating a change in the fill level of the reducing agent solution to a control unit.

7. The reducing agent tank as claimed in claim 6, wherein the control unit determines a misfilling of the reducing agent tank based at least in part on the measured conductivity of the inflowing liquid.

8. The reducing agent tank as claimed in claim 7, wherein the control unit is configured to initiate countermeasures for the protection of the exhaust-gas aftertreatment system based on the determination of the misfilling of the reducing agent tank.

* * * * *